(12) United States Patent
Thoren et al.

(10) Patent No.: US 6,452,064 B1
(45) Date of Patent: Sep. 17, 2002

(54) METHOD OF PRODUCING AN APERTURED COVERING SHEET FOR AN ABSORBENT ARTICLE AND A MATERIAL PRODUCED IN ACCORDANCE WITH THE METHOD

(75) Inventors: Agneta Thoren, Landvetter; Bror-Inge Helmfridsson, Partille, both of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/445,580

(22) PCT Filed: Jun. 18, 1998

(86) PCT No.: PCT/SE98/01187

§ 371 (c)(1), (2), (4) Date: Dec. 13, 1999

(87) PCT Pub. No.: WO99/00082

PCT Pub. Date: Jan. 7, 1999

(30) Foreign Application Priority Data

Jun. 27, 1997 (SE) ................................................. 9702509

(51) Int. Cl.[7] .............................................................. A61F 13/15
(52) U.S. Cl. ..................................... 604/383; 604/358
(58) Field of Search ............................ 604/385.01, 383, 604/585.01, 358

(56) References Cited

U.S. PATENT DOCUMENTS

| | | | |
|---|---|---|---|
| 4,323,069 A | 4/1982 | Ahr et al. .................... 128/287 |
| 4,342,246 A | 8/1982 | Rhodes et al. ............... 84/1.04 |
| 4,342,314 A | 8/1982 | Radel et al. ................. 128/287 |
| 4,397,644 A | 8/1983 | Matthews et al. .......... 604/378 |
| 4,634,440 A | 1/1987 | Widlund et al. ............ 604/383 |
| 4,690,679 A | 9/1987 | Mattingly, III et al. ..... 604/383 |
| 4,820,294 A | 4/1989 | Morris ........................ 604/383 |
| 5,171,238 A | 12/1992 | Kajander ..................... 604/383 |
| 5,728,085 A | 3/1998 | Widlund et al. ............ 604/378 |
| 5,730,737 A | 3/1998 | Widlund et al. ............ 604/378 |
| 5,814,034 A | 9/1998 | Widlund et al. ............ 604/367 |
| 5,817,085 A | 10/1998 | Widlund et al. ............ 604/379 |

FOREIGN PATENT DOCUMENTS

| | | |
|---|---|---|
| EP | 0 165 807 | 12/1985 |
| EP | 0 214 608 | 3/1987 |
| EP | 0 235 309 | 9/1987 |
| EP | 0 409 535 | 1/1991 |
| JP | 3-56 A | 1/1991 |
| SE | 510 531 | 5/1999 |

Primary Examiner—Rodney M. Lindsey
Assistant Examiner—Angela J. Grayson
(74) Attorney, Agent, or Firm—Burns Doane Swecker & Mathis, L.L.P.

(57) ABSTRACT

A method of manufacturing a fluid permeable covering sheet (9) for an absorbent article such as a diaper, a sanitary napkin, an incontinence protector or the like, wherein heated needles (4) are brought to penetrate a sheet of textile material (1) comprising at least one thermoplastic component, whereby the thermoplastic component closest to the needles (4) melts, whereafter the needles (4) are removed and the heated material (1) is passed through at least one nip of rollers (7) so that the thermoplastic component closest around the apertures is smoothed out into a substantially smooth material surface around the apertures, whereafter the thermoplastic component is brought to solidify. The invention further pertains to an apertured covering sheet (201, 301) for an absorbent article manufactured in accordance with the method, and an absorbent article (300) provided with a covering sheet manufactured in accordance with the method.

21 Claims, 3 Drawing Sheets

METHOD OF PRODUCING AN APERTURED COVERING SHEET FOR AN ABSORBENT ARTICLE AND A MATERIAL PRODUCED IN ACCORDANCE WITH THE METHOD

TECHNICAL FIELD

The present invention relates to a method of producing an apertured covering sheet for an absorbent article such as a diaper, a sanitary napkin, an incontinence protector, or the like, wherein heated needles are caused to penetrate a sheet of material comprising at least one thermoplastic component, and wherein the temperature of the needles during penetration of the sheet of material exceeds the melting temperature of the thermoplastic component.

The invention also concerns an apertured covering sheet for an absorbent article manufactured in accordance with the method, and an absorbent article provided with a covering sheet manufactured in accordance with the method.

BACKGROUND OF THE INVENTION

High demands on softness as well as dryness are put on fluid permeable covering sheets for absorbent articles of the kind which during use are intended to be in contact with the body of a user.

However, it has proven difficult to accomplish a fluid permeable covering sheet having a soft, textile-like surface which remains dry even after repeated wetting when the covering sheet is being used on an absorbent article.

In order to achieve a soft, textile-like covering sheet, it is common to use nonwoven materials. In order to more quickly lead fluid through the surface material down into a lower, absorbent material layer, it is common to perforate the material.

One such perforated nonwoven material is previously known through, for instance, EP 0,235,309. The perforated nonwoven material consists of a spunlace material having a high percentage of hydrophobic fibres. In a spunlace process, holes are formed in a fibrous material by ejecting very high pressure water jets against the material. The spunlace material is one of two layers in a topsheet-laminate and is intended to be the layer which during use is arranged closest to the user. The spunlace material consists of a higher percentage of hydrophobic fibres than the lower material layer in the topsheet. Thereby, the lower layer can drain liquid from the upper layer.

However, one problem with the described material is that holes which are formed by water jets become irregular both in shape and in size and exhibit fibres protruding from the edges of the holes, into the holes. Such protruding fibres diminish the area of the holes and will in addition act as wicks which transport liquid into the material between the holes by capillary action. The protruding fibre ends and the irregular shape and size of the holes considerably increase the risk of liquid remaining in the covering layer after wetting. Since a very small amount of liquid is sufficient for a surface material to be perceived as wet, this is evidently a considerable disadvantage with the known surface material.

A further problem with the described nonwoven material is that it is difficult to create a predetermined, well-defined hole-size. It is well known, for instance through EP 0,409, 535, that the hole dimensions of a perforated material are of determining significance to obtaining an optimal inflow of liquid. For nonwoven material exhibiting some areas having a dense fibre structure and other areas having an open fibre structure, this implies that it is difficult to obtain a uniform hole size. This is due to the fact that the holes in the dense fibre areas are smaller, since they are surrounded by more fibres. Moreover, such an apertured nonwoven material exhibits a relatively low tensile strength, since the aperturing involves a decrease in the strength of the material. Since it is important that the material has sufficient strength so that no risk of breaking exists either in connection with the aperturing process, during production of the absorbent article, or during use of the finished absorbent article, naturally the decrease in the strength of the material which accompanies the aperturing is a problem.

In EP 0,214,608 a nonwoven material is apertured using hot needles which heat the nonwoven material to a temperature which is somewhat below the melting point of the material. The holes which are thus created in the material are surrounded by an edge exhibiting a densified fibre structure. The previously mentioned problems with varying hole sizes and reduced material strength are partially solved with a material which is apertured in this manner. However, the problem with liquid spreading in the nonwoven and staying in its fibre structure still remains. The denser fibre structure around the holes is intended to absorb liquid in order to transport liquid through the holes into a material layer below. However, there is a risk that a portion of the liquid is left in the denser hydrophilic fibre structure surrounding the holes. Further, liquid may spread horizontally in the plane of the nonwoven material in the fibre capillaries in the nonwoven material. Since, during use, the nonwoven material is in direct contact with the skin of the user such spreading of liquid is, of course, extremely inconvenient.

In SE 9601681-1, nonwoven material is apertured with hot needles which heat the nonwoven material to a temperature exceeding the melting temperature of at least one component in the material. Accordingly, the holes which are thus created in the material are surrounded by an edge which is at least partially melted. The melted hole edge reduces horizontal spreading of liquid via the fibre capillaries, in the plane of the nonwoven material. However, it is possible to further improve the fluid pervious covering layer as disclosed in SE 9601681-1 in order to obtain a cover exhibiting both high softness and high surface dryness. Other examples of sanitary napkins including at least one layer with a plurality of apertures are given in EP 0,165,807 and U.S. Pat. No. 4,690,679.

DESCRIPTION OF THE INVENTION

The problem with accomplishing a fluid pervious topsheet for absorbent articles, which topsheet is soft and comfortable against skin and still exhibits high surface dryness has been substantially removed by the present invention.

Accordingly, the invention provides an apertured covering sheet exhibiting high softness as well as dryness against the skin of a user.

This is accomplished in accordance with the invention by means of heated needles which are caused to penetrate a sheet of textile material comprising at least one thermoplastic component, wherein the temperature of the needles during penetration of the sheet of material exceeds the melting temperature of the thermoplastic component. The heated needles melt the thermoplastic component closest to the needles whereafter the needles are removed and the heated material is passed between at least one pair of compression rollers whereby the thermoplastic component immediately surrounding the apertures is smoothed out in the plane of the sheet of material so that a substantially smooth material surface is formed around each aperture. The thermoplastic component is then solidified.

One advantage with an apertured sheet of material produced in accordance with the invention is that it exhibits high smoothness in the plane of the material. This means that the risk of the edges of the apertures in the covering sheet rubbing against the skin of the user is practically eliminated. A further advantage with the apertured sheet of material is that the surrounding, substantially melted edge of the apertures to a higher degree can be relied upon to constitute a continuous, liquid impermeable surface. Due to the fact that the thermoplastic material surrounding the apertures in the textile material is in a molten or at least softened state when the material is passed between the compression rollers, the molten or softened thermoplastic material is pressed into and fills out cavities between optionally occurring non-thermoplastic fibres in the textile material.

A further advantage of thermally aperturing the material so that the structure surrounding the apertures melts, and thereafter passing the material through the nip of a pair of rollers is that a specific aperture size is obtained with a high degree of repeatability.

The optimal aperture size varies with the intended use for the covering sheet. Menses and urine, for instance, have completely different surface energies and different Theological properties, which means that the design of the covering layer must be adapted accordingly. However, in a covering material in accordance with the invention, the shape and size of the apertures deviate only to a minimal degree from the intended optimal shape and size which has been decided with regard to the intended use for the covering material. Consequently, in accordance with the invention, well performing covering materials can be created for a wide range of different absorption purposes with great accuracy and repeatability.

Another advantage with passing the material through the nip of a pair of rollers directly after the aperturing step so that a substantially two-dimensional, flat material structure is created, is that the material demands less space when transported or stored. Moreover, it is possible to manufacture very thin absorbent articles when using such a covering material.

In accordance with one embodiment of the invention, the needles are of different size in the thickness dimension which means that a covering sheet which is apertured with such needles exhibits apertures having different aperture sizes. In accordance with an advantageous embodiment, when the apertured covering sheet is used as a fluid permeable covering sheet for a sanitary napkin, the apertures are of two different sizes. The larger apertures exhibit a diameter which is between 2–4.5 mm and the small apertures exhibit a diameter which is between 0.1–2 mm. For the larger apertures which preferably have a diameter greater than 2 mm this implies that a comparatively large amount of fibrous material must be eliminated from the aperture itself during the aperturing procedure. A small amount of material is evaporated due to the heat to which the material is exposed by the hot needles. The remaining amount of material will mainly attach itself to the edge of the created aperture where it forms a fluid impermeable edge. The total length of the edge of the aperture, which is the same as the circumference of the aperture, increases exponentially with a factor of two with regard to the radius of the aperture. This means that the larger the apertures in the material are, the more material per length unit is gathered along the edge of the aperture than for the smaller apertures.

When using the apertured covering layer as a fluid permeable covering layer positioned closest to a user, the edges of the apertures may irritate the skin. The edges of the apertures may irritate the skin both if the apertures are arranged over all of the surface of the covering layer and if the apertures are arranged only within limited areas such as, for instance, within the area of the article which is expected to be initially wetted by body fluid. In order to eliminate the problem with thick material edges, the flat-rolling of the covering layer after the aperturing is essential. Furthermore, for reasons which are explained in the above discussion, the flat-rolling is particularly important for covering layers exhibiting relatively large apertures.

In accordance with another embodiment, the distance between the needles is different within different areas of the covering layer whereby the sheet of material after the aperturing step exhibits areas with different spacing between the apertures. The advantage with such an embodiment is that it is possible to have the apertures more closely spaced within the area which is expected to receive the greatest amount of fluid and further apart along the longitudinal and transverse outer edges of the article.

In accordance with yet another embodiment, the sheet of material is passed through the nip between the rollers together with at least one additional fluid pervious sheet of material whereby the melted component surrounding the apertures in the apertured sheet of material adheres to the additional sheet of material. After passage through the nip between the rollers, the melted component is caused to solidify whereby the additional sheet of material is laminated to the apertured sheet of material. This embodiment is advantageous since a particular laminating step is eliminated. Usually, sheets of material are laminated using adhesive or by welding, such as, for instance, ultrasonic welding. However, a problem in connection with adhesive lamination is that the adhesive often penetrates the covering sheet so that a portion of the adhesive will be in direct contact with skin during use. This problem is also more pronounced when using covering layers having a large open area. In accordance with this embodiment the problem that an adhesive coating often causes reduced fluid wicking and acquisition is also avoided. A further advantage is that the production cost is reduced since no adhesive or additional process-step such as a welding step is needed.

In accordance with one embodiment, the additional sheet of material consists of a hydrophilic sheet of nonwoven. The advantage with such an embodiment is that the hydrophilic sheet of nonwoven absorbs fluid from the apertured sheet of material. Consequently, the apertured covering is efficiently drained of fluid.

The invention further concerns a fluid pervious covering layer which is produced according to the method for use in an absorbent article such as a diaper, an incontinence protector, a sanitary napkin, or the like. Accordingly, the fluid pervious covering layer comprises at least one apertured textile sheet of material comprising at least one thermoplastic component. The apertured sheet of material exhibits a substantially two-dimensional structure having a plurality of apertures each surrounded by a substantially fluid impervious edge consisting of a substantially smooth plastic surface in the plane of the material.

The apertured sheet of material preferably consists of a nonwoven material but may, of course, alternatively consist of other textile materials. As has been previously mentioned, the smooth aperture edge is particularly advantageous for covering sheets which exhibit relatively large apertures, something that is common in sanitary napkins. However, such covering sheet are also suitable as apertured covering sheets for children's diapers and incontinence protectors. It is extremely important that fluid permeable covering sheets for children's diapers exhibit high softness and smoothness, since the skin of a child is sensitive and, moreover, is not protected by hair. Moreover, for incontinence protectors, particularly of the kind which is used by older people who are mostly bed-ridden, it is very important that the covering layer which is closest to the user does not irritate the skin since wounds which may arise take a very long time to heal.

In accordance with one embodiment, the fluid permeable covering sheet comprises at least two layers of material. One advantage with a further layer of material which is positioned between the absorbent core in an absorbent article and the upper material layer positioned closest to the user is that such a layer may prevent superabsorbent particles or granules which come loose from the absorbent structure from spreading further out of the article. In addition to the fact that a reduced amount of superabsorbent material will lower the absorption capacity of the absorbent structure, the granules may also cause skin irritation when they come into direct contact with skin. A further layer of material will also serve to mask fluid which has been absorbed into the article, whereby the visual impression of, for instance, menstrual blood in a sanitary napkin does not appear as prominent as when using a single layer of material.

Still another embodiment of a fluid permeable covering sheet produced in accordance with the invention comprises a first layer of material and a second layer of material wherein the second layer of material is more hydrophilic than the first layer of material. The advantage with such an embodiment is that the second layer of material, which is more hydrophilic, will absorb fluid from the first layer of material and thereby improve the surface dryness of the cover. The second layer of material, which is more hydrophilic, also acts as a wicking layer, resulting in a more even distribution of fluid in an absorbent core arranged inside the cover. A fluid distribution layer also makes it possible to achieve a higher level of exploitation of the total absorption capacity of the absorbent core, which reduces the risk of fluid leakage.

In accordance with one embodiment, the second layer of material is non-perforated. The advantage with a non-perforated second layer of material is that a non-perforated layer increases the tensile strength of the covering sheet. A high tensile strength in the covering sheet is of importance during production of the covering sheet itself, during production of the absorbent article and, finally, during use of the produced article. However, it is possible to use a second layer of material exhibiting perforations.

The invention also includes an absorbent article such as a sanitary napkin, a diaper, an incontinence protector, or the like, comprising an absorbent core enclosed within a cover, wherein at least a portion of the cover consists of a fluid permeable covering sheet. The covering sheet is characterised in that it exhibits a substantially two-dimensional, flat structure. In addition, the covering sheet comprises at least one layer of material exhibiting a plurality of apertures. Each of the apertures is surrounded by a substantially fluid impermeable edge exhibiting a substantially smooth plastic surface in the plane of the material. Accordingly, the material exhibits the softness and textile feel of a nonwoven material at the same time as the smooth plastic surfaces around the apertures create a material exhibiting similarities with a perforated plastic film with regard to the ability of maintaining a high surface dryness.

SHORT DESCRIPTION OF FIGURES

The invention will in the following be more closely described with reference to the embodiments which are shown in the appended drawings.

DETAILED DESCRIPTION OF EMBODIMENTS

Figure 1A:
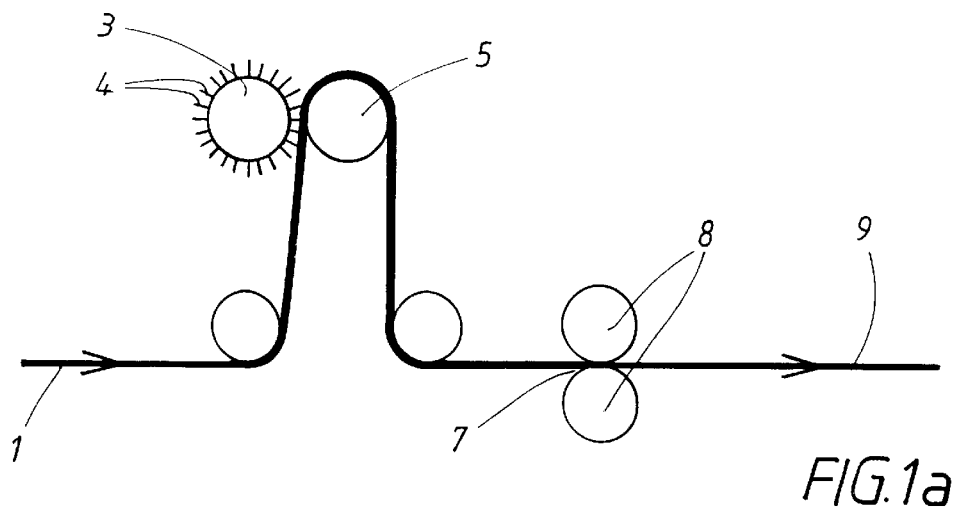
FIGS. 1a and 1b show a cross section of the equipment which is used when producing covering sheets in accordance with the invention.
Figure 1B:
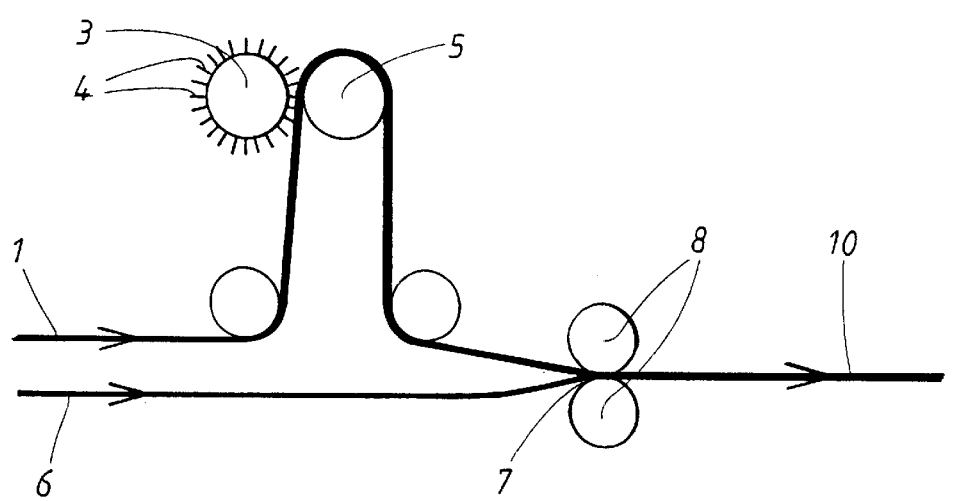

In FIGS. 1a and 1b are schematically shown two somewhat different ways of producing fluid permeable materials intended for use as fluid permeable covering sheets on absorbent articles.

In the method of manufacturing which is illustrated in FIG. 1a, a web of material consisting of a textile material 1 is continuously fed between a pair of rollers 3,5 comprising a needle roller 3 and a counter roll 5. The needle roller exhibits a plurality of heated needles 4, protruding radially from the needle roller 3 and being heated by one or more electrical cartridges which are arranged in the cylindrical space inside the needle roller. In order to heat the needles 4, it is further possible to expose the needle roller to infrared heat. In order to obtain a desired temperature in the needles 4, a combination of the said heating methods is preferably used. Naturally, it is also possible to use other available methods in order to achieve the desired temperature in the needles 4. The textile material 1 comprises fibres having a fibre surface which at least partly consists of a thermoplastic material. Suitable textile materials for the purpose are, for instance, nonwoven materials wholly or partially consisting of thermoplastic fibres such as polyethylene or polypropylene or bicomponent fibres comprising a thermoplastic component. Although nonwoven materials are preferred, it is, of course, possible to use other types of textile materials such as woven, knitted or crocheted materials.

The hot needles 4 are heated to a temperature which exceeds the melting temperature of the thermoplastic component in the textile material 1. When the textile material passes between the needle roller 3 and the counter roll 5, the material is penetrated by the needles 4, whereby the thermoplastic component in the material 1 melts in the vicinity of the needles 4. The apertured textile material 1 is subsequently passed into the nip 7 between two compression rollers 8. Because the thermoplastic material surrounding the apertures in the textile material is still hot and therefore is in a melted, or at least softened state, the calendering in the roller nip 7 between the compression rollers 8 creates a substantially smooth, flat, ring-shaped plastic surface surrounding each aperture in the textile material. The melted, or softened thermoplastic material is pressed into and fills out cavities between any occurring non-thermoplastic fibres or fibre-components in the textile material, whereby the fibre structure around the apertures disappears. After passage between the calender rollers 8, the formed covering material 9 is left to cool at room temperature, or is cooled at a temperature below room temperature.

By the provision of a fluid impermeable plastic edge surrounding the apertures in the covering material 9, fluid transport in a direction away from the edges of the apertures into the fibrous portions of the covering material is prohibited when the covering material 9 is used as fluid permeable covering layer on an absorbent article.

FIG. 1b shows the manufacturing process for a covering material 10, which, apart from a sheet of material 1 which is perforated by hot needles 4 arranged on a needle roller 3, comprises a second, fluid permeable sheet of material 6.

In the example which is being shown, the still warm sheet of textile material is passed into a roller nip 7, between two compression rollers 8 together with the second sheet of material 6. When the thermoplastic component in the perforated sheet of material 1 is brought to cool after the compression step, the thermoplastic component is solidified. Thus, the two sheets of material 1,6 are bound together into a covering laminate 10. The material in the second sheet of material 6 in the laminate 10 may be of any kind suitable for the purpose as long as it is fluid permeable. Preferred materials are nonwoven, perforated plastic film, or netting. If the second sheet of material 6 is intended to be facing the absorption core in an absorbent article, it is suitable to use a hydrophilic second sheet 6, which preferably exhibits a higher hydrophilicity than the first sheet of material 1.

It is, of course, possible to produce covering laminates 10 comprising more than two layers in the way shown in FIG. 1b. One sheet of material may, for instance, be placed on each side of the perforated sheet of material 1. Further, two or more sheets of material may be arranged on the same side of the perforated sheet of material 1. However, in the latter case it is necessary that the sheet of material which is perforated with hot needles primarily consists of thermoplastic material so that a sufficient amount of thermoplastic material is available in order to permit the sheets of material to be bonded together. The number of sheets of material which may be joined together depends, apart from the proportion of thermoplastic material in the perforated textile sheet of material, also on the thickness of the different sheets. An upper limit for the number of layers which may be bound together with the method shown in FIG. 1b is approximately 4–5 layers.

Furthermore, it is possible to let two or more sheets of material, at least one of which comprises thermoplastic material, pass between the needle roller 3 and the counter roll 5 in the production methods shown if FIGS. 1a and 1b. In this manner, a finished covering laminate is obtained having at least two perforated layers of material.

Figure 2:
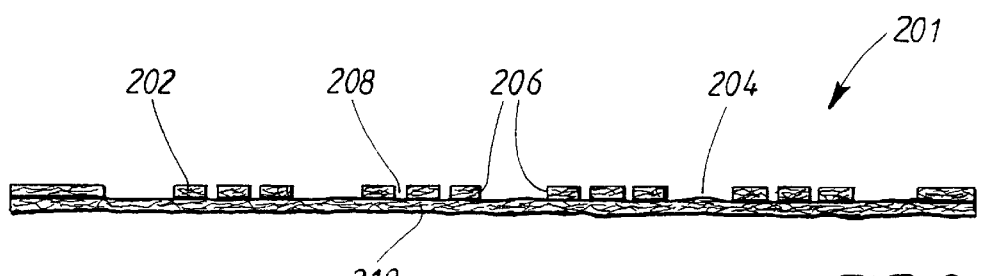
FIG. 2 shows a cross section of a covering sheet produced in accordance with the invention.

FIG. 2 shows a covering material 201 consisting of a first sheet of material 202 and a second sheet of material 210. The first sheet of material 202 has been perforated with hot needles, as is shown in FIGS. 1a and 1b. The second sheet of material 210 has been laminated together with the first sheet of material in a compression step following on the perforation step, as is shown in FIG. 1b.

The different layers being part of the covering material 201 may be nonwoven materials of different types or composition. A nonwoven material gives the covering material 201 a soft, pleasant surface which does. not chafe or otherwise irritate the skin. However, it is also possible to use one or several layers of plastic film, net material, or the like. The apertured sheet of material 202 comprises at least one heat meltable component which may exist in the form of complete fibres, in the form of a part component in a so-called bicomponent fibre, or in the form of a film material. Suitable heat meltable materials for the purpose are polyethylene, polypropylene, or polyester. The heat meltable component constitutes at least 55% by weight of the textile material, at least within the perforated area. The heat meltable component preferably constitutes at least 70% by weight of the textile material. Further, it is possible that the sheet of material 202 consist solely of thermoplastic material. The sheet of material 202 exhibits a plurality of penetrating apertures 204,208. The apertures 204,208 exhibit two mutually different aperture sizes. The larger apertures 204 are preferably fewer in number and the smaller apertures 208 are preferably more numerous. Apertures having two mutually different aperture sizes have been formed by bringing hot needles of two different thicknesses to penetrate the sheet of material 202. The temperature of the needles has exceeded the melting temperature of the heat meltable component in the sheet of material 202. Due to a sufficiently high proportion of material which melts as a result of the penetration of the covering layer, the finished material has a substantially fluid impermeable edge 206 surrounding each aperture. The fluid impermeable edge 206 increases the tensile strength of the covering layer and prevents fluid from spreading from the aperture edge 206, out over the surface of the covering layer 201. The fluid barrier effect is due to the fact that no free fibre ends are present around the apertures, which might have caught fluid and led it, through capillary action, in a wrong direction away from the aperture 204.

Figure 3:
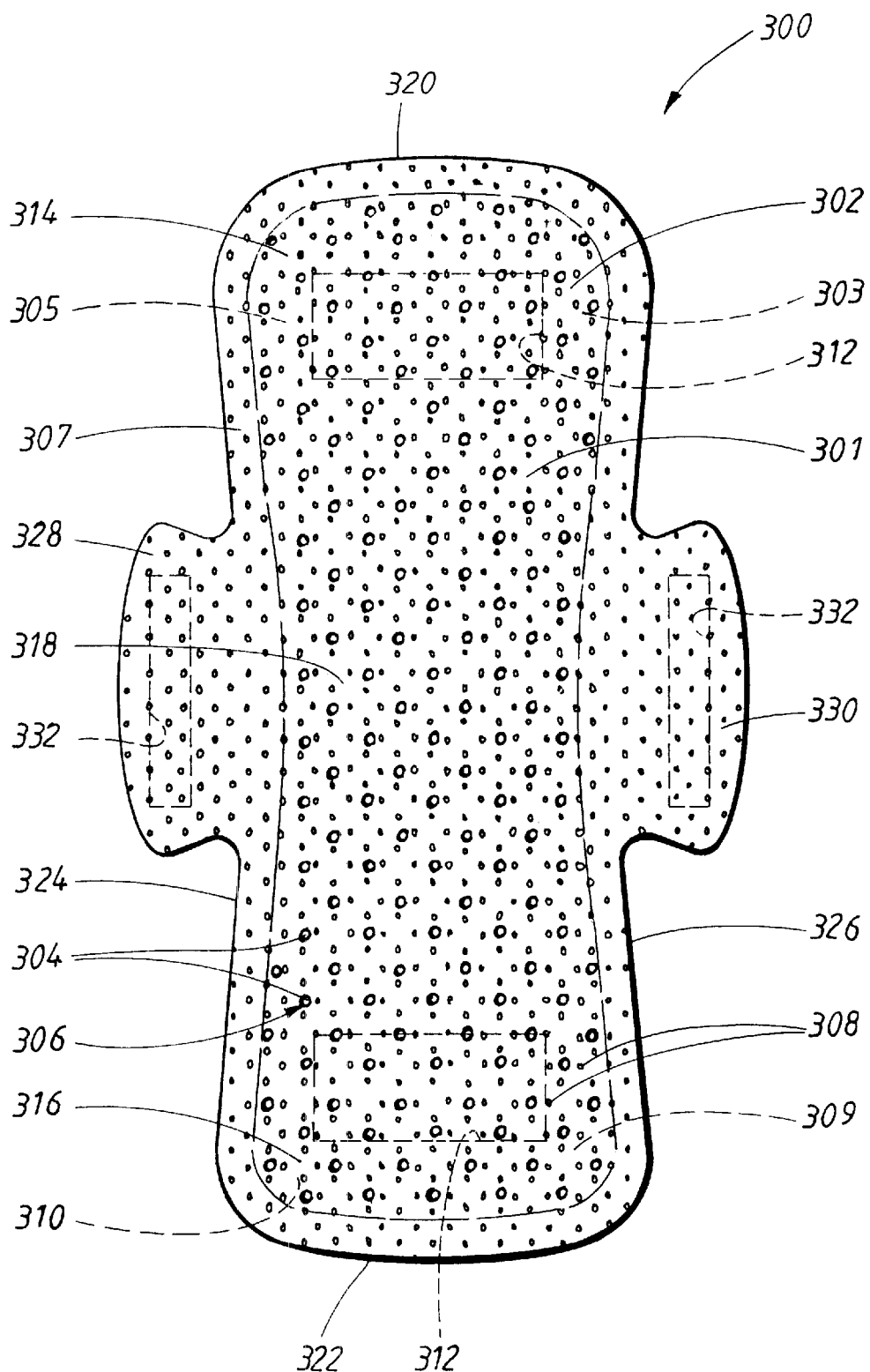
FIG. 3 shows a sanitary napkin having a fluid permeable covering sheet in accordance with the invention, viewed from the side which during use is intended to be facing a user.

The sanitary napkin 300, shown in FIG. 3 comprises a first fluid permeable covering layer 301, in accordance with the invention, a fluid impermeable covering layer 303, and an absorption core 305 enclosed between the covering layers 301,303. The fluid impermeable covering layer 303 may consist of a fluid impermeable plastic film, a nonwoven sheet which has been coated with a fluid barrier material, or some other flexible sheet of material which resists fluid penetration. It is generally advantageous if the fluid impermeable covering layer 303 has a certain degree of breathability, that is, will permit the passage of water vapour. The two covering layers 301,303 have a somewhat larger extension in the plane than the absorption core 305 and extend a distance past the edges of the absorption core 305, around the entirety of its periphery. The covering layers 301,303 are joined to each other within the extending portions 307, for instance by gluing, or welding with heat or ultrasonically.

The absorption core 305 is usually constructed of one or more layers of cellulose fibres, for instance fluffed cellulose pulp. An example of an absorbent structure which is suitable for the purpose is found in WO 94/10956, which publication describes an absorbent material which is cut from a web of material without preceding defibration and mat-forming steps. The material increases the surface dryness of the resulting article, which is a particular advantage when the fluid permeable covering layer 301 has a textile sheet of material closest to the user. A high absorbent capacity means efficient draining of fluid from upper layers of material.

In addition to cellulose fibres, the absorption core 305 may also contain superabsorbent material, i.e. material in the form of fibres, particles, granules, film or the like, which has the ability to absorb fluid corresponding to several times the weight of the superabsorbent material itself. A superabsorbent material binds the absorbed fluid and forms a fluid-containing gel. The absorption core 305 may further contain binders, shape stabilising components, or the like. Additional absorption layers which improve the absorption properties may also be used, such as different types of wicking inserts, or material layers. The absorbent core 305 may be chemically or physically treated to alter the absorption properties. It is, for instance, common to arrange compressed areas in an absorption layer in order to control the fluid flow in the absorbent core 305. Moreover, other types of absorption materials may be utilised, alone or in combination with cellulose fibres and superabsorbent material.

Some examples of useful absorbent materials are absorbent nonwoven materials, foam, or similar.

On the outside of the fluid impermeable covering layer 303 is arranged a fastening means in the shape of two areas 312 of self-adhesive glue. Before use, the adhesive areas 312 are preferably covered by removable protection sheets of release-coated paper, or plastic film, which are not shown in FIG. 3. A number of adhesive patterns other than the ones which are shown are, of course, conceivable, as well as other kinds of fastening means such as hook-and-loop surfaces, press-studs, girdles, special underpants, or the like. A sanitary napkin of the kind shown in FIG. 3 is attached inside an ordinary pair of underpants during use. The fastening means should naturally be of a kind which permits removal of the sanitary napkin from the underpants without causing damage thereto.

The sanitary napkin 300 is hourglass-shaped, having somewhat broader end portions 314, 316 and a somewhat narrower crotch portion 318 located between the end portions 314, 316. The crotch portion 318 is the portion of the sanitary napkin which is intended to be placed in the user's crotch during use and serve as a receiving surface for the body fluid which is discharged to the sanitary napkin. Furthermore, the sanitary napkin exhibits two transversely extending end edges 320,322, and two longitudinally extending side edges 324,326, running between the end edges 320,322.

In the example which is shown, the sanitary napkin is further provided with fastening flaps 328,330, which are formed of the two covering layers 301,303 and which extend from the side edges 324,326 of the sanitary napkin 300 at the crotch portion 318. The fastening flaps 328,330 are intended to be folded around the leg edges of the user's underpants during use of the sanitary napkin and to be attached to the outside of the underpants. For this purpose, the fastening flaps 328,330 are provided with special fastening means 332, which may be chosen in the same way as the fastening means 312 on the fluid impermeable covering layer 303.

The fluid permeable covering layer 301 consists of a first layer of material 302 and a second layer of material 310. The first layer of material 302 exhibits a plurality of penetrating apertures 304,308. The apertures 304, 308 have two different aperture sizes. The larger apertures are preferably fewer in number than the smaller apertures 308. The small apertures 308 are evenly distributed over the entire surface of the covering layer 301. Furthermore, the area of the first layer of material 302 which covers the absorption core 305 on the inside of the covering layer, also exhibits large apertures 304 evenly distributed over this area. Accordingly, the first layer of material 301 exhibits both large and small apertures 304,308 within all of that portion of the sanitary napkin which has an absorbent core 305 on the inside and only small apertures within the remaining portions of the surface of the covering layer 301. It is, of course, also possible to use a first layer of material exhibiting apertures of only one size, or apertures of more than two sizes.

The first layer of material 302 consists of a textile material which, during use of the sanitary napkin, is intended to be in contact with the body of the user. The layer of material 302 consists, at least partially, of a material which is heat meltable. The heat meltable material has, during forming of the apertures 304 in the layer of material 302, been melted in the area closest to each aperture 304. Before the melted material is solidified, the material is passed through at least one nip of rollers so that the heat meltable component closest to the apertures is smoothed out, causing the material surrounding the apertures to exhibit a smooth plastic surface in the plane of the material. The continuous, plastic-like surface surrounding the apertures forms a substantially completely fluid impermeable edge around the whole periphery of the aperture 304. Moreover, as has been previously mentioned, the continuous edge 306 increases the tensile strength of the covering material 301. In addition, the edge 306 prevents fluid from spreading from the apertures out into the covering layer 302. Instead, body fluid which impinges upon the sanitary napkin 300 passes down through the apertured layer of material 302 to the second layer of material 310 and then further down into the absorption core 305 which is located inside this layer. Moreover, the risk of the aperture edges being perceived as chafing against skin is reduced due to the layer of material 302 having been passed through a nip of rollers.

The second layer of material 310 of the fluid permeable covering layer 302 is arranged inside the first layer of material 302. Accordingly, the second layer of material 310 is located between the first layer of material 302 and the absorption core 305 of the sanitary napkin. The second layer of material 310 consists of a material which is more hydrophilic than the first layer of material 302, whereby fluid transport will take place in a direction towards the absorption core 305 of the sanitary napkin. Some examples of suitable material for the second layer of material 310 are different types of nonwoven materials, air-laid or wet-laid cellulose layers, wadding of different kinds, foam materials, or the like. Further, it is possible that the second layer of material consists of a laminate consisting of, for instance, an air-laid cellulose layer and a layer of thermo-fibres. The second layer of material may also be a laminate of a cellulose layer and a thermo-bonded or latex-bonded nonwoven. Furthermore, it is also possible to use other laminates, or so called combination materials as a second layer of material 310.

In order to facilitate fluid transfer between the fluid permeable covering layer 301 and the absorption core 305, it is suitable to arrange the second layer of material 310 in direct contact with the absorption core 305. The layer of material 310 is preferably joined to the absorption core 305 by adhesive, welding, needling, or similar. It is also conceivable that the covering layer 301 of the sanitary napkin only consists of a single layer of material, i.e. the first layer of material 302, which in that case is in direct contact with the absorption core 305.

Figure 4:
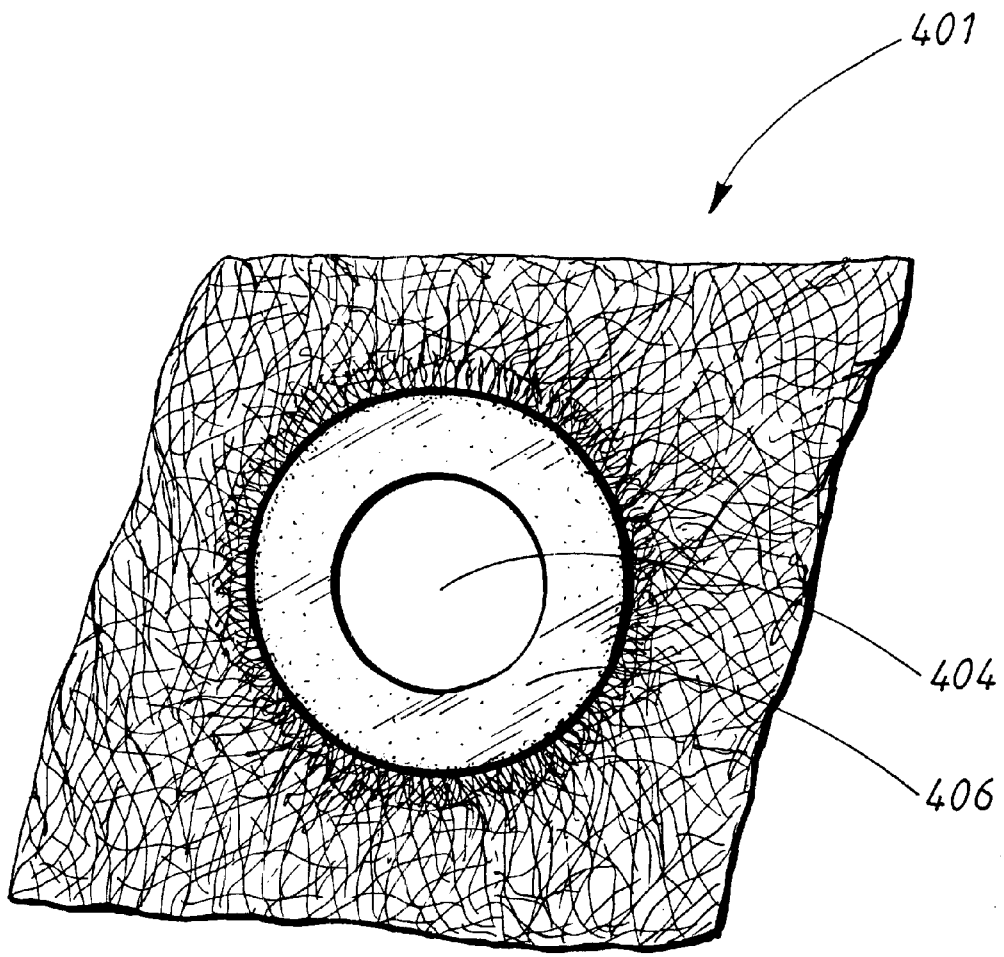
FIG. 4 shows an enlarged view of a piece of a covering sheet having an aperture surrounded by a flattened material edge.

FIG. 4 is a greatly enlarged view showing the appearance of an aperture 404 in a piece of covering material 401. It is evident that the material surrounding the aperture 404 and forming the fluid impermeable edge 406 exists in the form of a substantially flat, smooth surface after melting and rolling of the material. As the material is melted round the apertures, its fibrous structure is lost and the subsequent rolling causes the fluid impermeable edge to be of a character comparable to a plastic film.

The invention shall not be considered to be restricted to the embodiments described herein. Accordingly, a number of further variants and modifications are conceivable within the scope of the appended claims.

The invention is also intended to encompass all conceivable combinations of the described embodiments.

What is claimed is:

1. A method of producing a fluid permeable covering sheet for an absorbent article, said method comprising:

creating apertures in a sheet of a fibrous textile material, said fibrous textile material comprising at least one thermoplastic component, the apertures being created by bringing heated needles having a temperature exceeding the melting temperature of the thermoplastic component to penetrate the sheet of fibrous textile material, whereby the heated needles melt the thermoplastic component closest to the needles, whereafter the needles are removed from the sheet of fibrous textile material, and after creating the apertures, passing the heated fibrous textile material through at least one nip of rollers between two compression rollers, whereby the thermoplastic component closest around the apertures is smoothed out in the plane of the sheet of fibrous textile material so that a substantially smooth material surface is obtained around the apertures, whereafter the thermoplastic component is brought to solidify.

2. A method of producing a fluid permeable covering sheet in accordance with claim 1, wherein the apertured sheet of material includes a layer of nonwoven.

3. A method of producing a fluid permeable covering sheet in accordance with claim 1, wherein the needles exhibit at least two different thicknesses, whereby the apertures formed in the sheet of material exhibit at least two different aperture sizes.

4. A method of producing a fluid permeable covering sheet in accordance with claim 1, wherein the mutual distance between the needles is different within different areas of the covering sheet, whereby the covering sheet exhibits areas having different aperture spacing after the creating apertures step.

5. A method of producing a fluid permeable covering sheet in accordance with claim 1, wherein the sheet of material is passed through the nip of rollers together with at least one further fluid permeable sheet of material, whereafter the melted component is brought to solidify after passage through the nip of rollers such that the further sheet of material is joined to the apertured sheet of material.

6. A method of producing a fluid permeable covering sheet in accordance with claim 5, wherein the further sheet of material includes a hydrophilic sheet of nonwoven.

7. A method of producing a fluid permeable covering sheet in accordance with claim 1, wherein the absorbent article includes a diaper.

8. A method of producing a fluid permeable covering sheet in accordance with claim 1, wherein the absorbent article includes a sanitary napkin.

9. A method of producing a fluid permeable covering sheet in accordance with claim 1, wherein the absorbent article includes an incontinence protector.

10. A fluid permeable covering sheet for an absorbent article, said covering sheet comprising an apertured, textile sheet of a fibrous material comprising at least one thermoplastic component, wherein the covering sheet exhibits a substantially two-dimensional structure with a plurality of apertures, each of the apertures surrounded by an essentially fluid impermeable edge having an essentially smooth plastic surface in the plane of the material.

11. A fluid permeable covering sheet in accordance with claim 10, wherein the apertured sheet of material includes a nonwoven.

12. A fluid permeable covering sheet in accordance with claim 10, wherein the absorbent article includes a diaper.

13. A fluid permeable covering sheet in accordance with claim 10, wherein the absorbent article includes an incontinence protector.

14. A fluid permeable covering sheet in accordance with claim 10, where the absorbent article includes a sanitary napkin.

15. A fluid permeable covering sheet in accordance with claim 10, wherein the covering sheet comprises at least two layers of material.

16. A fluid permeable covering sheet in accordance with claim 15, wherein the covering sheet comprises a first layer of material and a second layer of material, and the second layer of material is more hydrophilic than the first layer of material.

17. A fluid permeable covering sheet in accordance with claim 15, wherein the second layer of material is non-perforated.

18. An absorbent article comprising:
an absorption core enclosed within a cover, wherein at least a portion of the cover comprises a fluid permeable covering sheet comprising a fibrous textile material, wherein the fluid permeable covering sheet includes at least one layer of material exhibiting a plurality of apertures, each of the apertures surrounded by an essentially fluid impermeable edge exhibiting an essentially smooth plastic surface surrounding the apertures in the plane of the material, and wherein the sheet of material has a substantially two-dimensional structure.

19. An absorbent article in accordance with claim 18, wherein the absorbent article includes a sanitary napkin.

20. An absorbent article in accordance with claim 18, wherein the absorbent article includes a diaper.

21. An absorbent article in accordance with claim 18, where the absorbent article includes an incontinence protector.

* * * * *